United States Patent [19]

Huang

[11] 4,368,201
[45] Jan. 11, 1983

[54] TETRAHYDRONAPHTHOXAZOLES

[75] Inventor: Fu-chih Huang, Boonton, N.J.

[73] Assignee: USV Pharmaceutical Corporation, Tarrytown, N.Y.

[21] Appl. No.: 285,216

[22] Filed: Jul. 20, 1981

[51] Int. Cl.³ .................. C07D 263/60; C07D 277/84; A61K 31/425
[52] U.S. Cl. .................................. 424/272; 548/217; 548/306; 548/150
[58] Field of Search ......................... 548/217; 424/272

[56] References Cited

U.S. PATENT DOCUMENTS 2,985,661  5/1961  Hein et al. ............................ 548/217
3,316,274  4/1967  Rauch et al. ......................... 548/217
4,298,742 11/1981  Brown et al. ........................ 548/217

OTHER PUBLICATIONS

Burger, A., "Medicinal Chemistry," 2nd Ed., 1960, pp. 496–497, Interscience Publishers, Inc., N.Y.

Primary Examiner—Donald G. Daus
Assistant Examiner—Sharon A. Gibson

[57] ABSTRACT

Compounds having the structure:

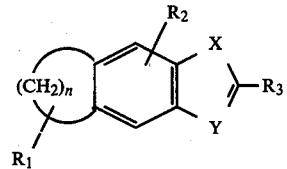

are novel and useful as antiallergic agents. The compounds are formulated with a pharmaceutical carrier for oral, parental, inhalational, or rectal means of administration.

12 Claims, No Drawings

TETRAHYDRONAPHTHOXAZOLES

This invention relates to heterocyclic compounds, more particularly to certain novel oxazole derivatives which possess useful pharmacological activity and/or are useful as intermediates in preparing such active compounds. The invention also includes processes for preparing the compounds of the invention.

Accordingly, the present invention provides novel compounds of the formula:

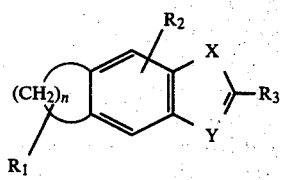

wherein
n is 3, 4, 5, or 6,
X is O, S, N, or C,
Y is C or N,
$R_1$ is H or alkyl,
$R_2$ is H, alkyl, hydroxyl, alkoxy, cyano, phenyl, carboxyl, tetrazole or halogen,
$R_3$ is CN, tetrazole, carboxamide or

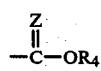

wherein
Z is O, S, or NH,
$R_4$ is H, alkali metal, ammonium or organic ammonium, alkyl, alkoxyalkyl, aryl, or aralkyl, and wherein the portion of the compound containing n may be carbocyclic or contain a hetero atom, or may be an aryl or heteroaryl ring.

In the preferred compounds n is 4, X is oxygen, Y is nitrogen, $R_1$ is hydrogen, $R_2$ is hydrogen or an alkyl having 1 to 6 carbon atoms, and $R_3$ is tetrazole or

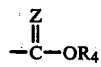

wherein Z and $R_4$ are defined as above. The alkyl groups of the compound contain 1-6 carbon atoms.

The compounds of FIG. 1 can be prepared by the following series of reactions

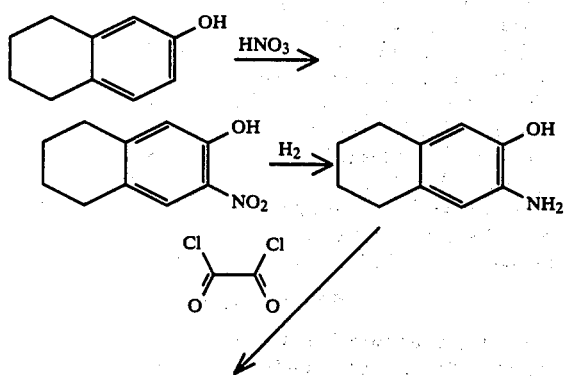

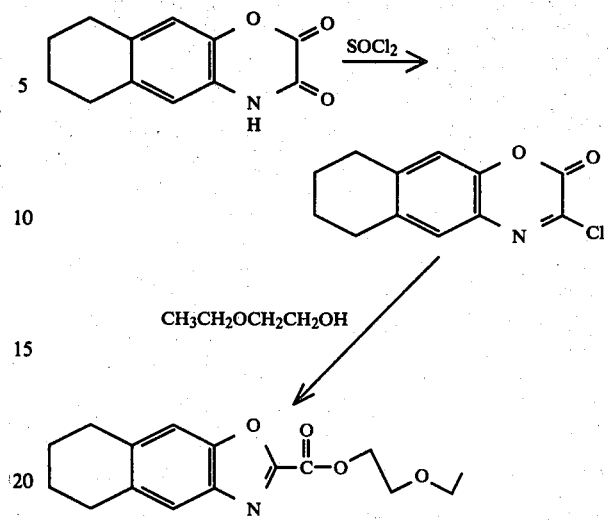

Other standard reactions known to those skilled in the art can be carried out to modify or introduce other functional groups.

The compounds of the present invention show strong activity as inhibitors of wheal formation in the passive cutaneous anaphylaxis (PCA) screen and as inhibitors of histamine release from passively sensitized rat mast cells (RMC), making them useful in the treatment of allergy. These standard procedures for the determination of antiallergy activity are described in the following literature references:

PCA: Nota, Life Sciences, I, 465 (1963), Ovary, Proc. of the Soc. of Exptl. Biol. and Med. 81, 584 (1952).

RMC: Kusner, et al., J. Pharmacol. and Exp. Ther. 184, 41 (1973).

The compounds exhibit $ED_{50}$ values of from 1.0 to 50.0 mg/kg on oral administration in the PCA screen and $I_{50}$ values of from 1 to 100 μm in the RMC screen. The compounds may be administered orally or parenterally in the treatment of allergies and related conditions, and it will be within the skill of the practitioner to determine the exact amount to be administered and the mode of administration.

EXAMPLE 1

A. 5,6,7,8-Tetrahydro-3-nitro-2-naphthol

To a solution of 5,6,7,8-tetrahydro-2-naphthol (44 g) in 300 ml of acetic acid was added dropwise fuming nitric acid (12 ml in 12 ml of acetic acid) over a period of 30 minutes. The reaction mixture was then stirred for an additional 5 hours at room temperature. After evaporation of the solvent, the crude product was purified by column chromatography (silica gel) to give 16 g of pure product, m.p. 88°–89° C.

B. 5,6,7,8-Tetrahydro-3-amino-2-naphthol

An ethanolic solution of the nitro compound (16 g in 200 ml EtOH) and 1 g of 5% Pd/C was hydrogenated at 40 psi overnight. DMF (80 ml) was added, and the reaction mixture then filtered. Evaporation of solvent gave 14 g of the desired compound.

C. 6,7,8,9-Tetrahydronaphth[2,3-b]-1,4-oxazine-2,3-(4 H)-dione

Seven grams of the above amino compound in 50 ml of toluene was added in four portions to a solution of 5.3 ml of oxalyl dichloride in 100 ml of toluene at 90° C. over a period of 30 minutes. The reaction mixture was then heated to reflux for 2 hours. After evaporation of solvent, the residue was recrystallized from ethyl acetate-toluene to give 9 g of dione (3), m.p. 262°–266° C. (dec.).

D. 6,7,8,9-Tetrahydro-3-chloro-naphth[2,3-b]-1,4-oxazine-3-one

A mixture of 8.5 g of the above dione and 3.7 ml of thionyl chloride in 150 ml of toluene and 1.5 ml of dimethyl formamide was refluxed for 2.5 hours. Evaporation of solvent gave 8 g of crude iminochloride which was used without further purification.

E. Ethoxyethyl-5,6,7,8-Tetrahydronaphth[2,3-d]oxazole-2-carboxylate

A mixture of the above iminochloride (4 g) and sodium bicarbonate (1.56 g) in 30 ml of ethoxyethanol was heated at 70° C. for 4 hours. After filtration the solvent was evaporated to dryness. The residue was purified by HPLC to give 1.5 g of white product, m.p. 57°–59° C.

EXAMPLE 2

Sodium 5,6,7,8-tetrahydronaph[2,3-d]oxazole-2-carboxylate

The ester from Example 1 [E], 1.2 g, was suspended in 5 ml of water and hydrolyzed with 4.1 ml of 1 normal NaOH at room temperature for 4 hours. After filtration, the crude product was suspended in 95% ethanol (20 ml) and filtered again to give 0.7 g of white solid product (m.p. 276°–278° C., dec).

EXAMPLE 3

A. 2-Cyano-5,6,7,8-tetrahydronaphth[2,3-d]oxazole

Chloral (10.7 g in 20 ml of water) and hydroxylamine hydrchloride (4.5 g in 10 ml of water) was added simultaneously to a solution of 5,6,7,8-tetrahydro-3-amino-2-naphthol (7 g) in 50 ml of water containing 3.8 ml of concentrated HCl at 60°–70° C. The reaction mixture was neutralized with sodium acetate (25 g) to keep the PH 4.5 over a period of 1 hour. The reaction mixture was cooled, filtered, and dried thoroughly to give 8.5 g of 5,6,7,8-tetrahydronaphth[2,3-d]oxazole-2-aldoxime as dark solid product.

B. The above oxime and 3.3 ml of thionyl chloride in 100 ml of toluene was refluxed for 2 hours. After filtration, the organic solvent was evaporated to give 5.5 g of 2-cyano-5,6,7,8-tetrahydronaphth[2,3-d]oxazole.

EXAMPLE 4

2-(5-Tetrazolyl)-5,6,7,8-tetrahydronaph[2,3-d]oxazole

A mixture of the cyano compound from example 3, (5.6 g), sodium azide (2.54 g), and ammonium chloride (2.16 g) in 120 ml of DMF was heated at 100° C. for 4 hours. The reaction mixture was treated with charcoal and filtered through celite. After evaporation of solvent, the residue was washed well with water and filtered. Recrystallization from DMF and water gave 1.1 g of 2-(5-tetrazolyl)-5,6,7,8-tetrahydronaphth[2,3-d]oxazole.

EXAMPLE 5

A. 5,6,7,8-Tetrahydronaphthyl-2-allyl ether

A mixture of 5,6,7,8-tetrahydronaphth-2-ol (29.6 g), potassium carbonate (50 g), allyl bromide (17.3 g) and sodium iodide (3 g) in 250 ml of acetone was refluxed overnight. More potassium carbonate (20 g), sodium iodide (7 g), and allyl bromide (10 ml) was added and the reflux was continued for an additional 30 hours. After filtration, the organic solvent was evaporated to dryness. The residue was taken into ether, washed with water, 1 N NaoH solution and dried over anhydrous magnesium sulfate. Concentration of the organic solution gave 37.8 g of 5,6,7,8-tetrahydronaphthyl-2-allyl ether.

B. Mixture of 1-allyl and 3-allyl-5,6,7,8-tetrahydro-2-naphthol

A boron trichloride-methylene chloride solution (123 ml, 1 M) was added dropwise to 35 g of the above ether in 1.5 l. of methylene chloride at −35° C. under nitrogen over a period of 1.75 hours. The reaction mixture was then warmed up to 10° C. in 2.5 hours and then kept at room temperature for 45 minutes. Methanol (100 ml) was added to the reaction mixture. After evaporation of organic solvent, the residue was taken into ether (500 ml), and the organic solution was washed with water and dried. Evaporation of organic solvent gave 34 g of product, as a mixture of two isomers. This was used for nitration without further purification.

C. 1-Allyl-3-nitro-5,6,7,8-tetrahydronaphth-2-ol

The isomeric mixture from above, 30 g, in 500 ml of ether was nitrated with 6.5 ml of fuming nitric acid in 100 ml of ether over a period of 2.5 hours at 10° C. After stirring at room temperature for an additional 4 hours, the reaction mixture was washed with water, 1 N NaHCo3 solution, and dried over anhydrous magnesium sulfate. Evaporation of solvent gave 36.5 g of crude products. The crude nitro products were then passed through two silica gel columns (600 g each, eluted with methylene chloride-Hexane, 2:3) to give 25 g of mixed nitro compounds. Recrystallization from hexane gave 15 g of pure 1-allyl-3-nitro-5,6,7,8-tetrahydronaphth-2-ol.

D. 1-Propyl-3-amino-5,6,7,8-tetrahydronaph-2-ol

The above nitro compound (13 g) and 1.3 g of 5% Pd-C in 300 ml of ethanol was hydrogenated at 40 psi for 2 hours. Filtration and evaporation of solvent gave 11.3 g of white solid, m.p. 91°–93° C.

E. 10-Propyl-6,7,8,9-tetrahydronaph[2,3-b]-1,4-oxazine-2,3-dione

A toluene solution of the above amine (11 g in 350 ml was added dropwise to a solution of 4.68 ml of oxalyl dichloride in 90 ml of toluene at 100° C. over a period of 2 hours. The reaction mixture was then refluxed for an additional 0.5 hour and then cooled down to room temperature. After filtration, the filtrate was concentrated to give 5.6 g of yellowish powder, m.p. 175°–180° C.

F. Iminochloride

A mixture of the above dione (5.5 g) and 1.8 ml of thionyl chloride in 200 ml of toluene was brought to reflux and then 0.73 g of DMF was added. The reaction mixture was refluxed for 0.5 hour. Evaporation of solvent gave 5.8 g of crude iminochloride.

G. Ethoxyethyl-9-propyl-5,6,7,8-tetrahydronaph(2,3-d)oxazol-2-carboxylate

The above iminochloride (5.8 g) and sodium bicarbonate 1.29 g in 50 ml of ethoxyethanol was heated at 90° C. for 20 hours. After evaporation of solvent, the residue was taken into ethyl acetate. The organic solution was then washed with water, 1 N HCl solution, saturated NaCl solution, and dried. Evaporation of solvent gave 5 g of dark crude oil. Purification by Hplc gave 700 mg of pure ethoxyethyl-9-propyl-5,6,7,8-tetrahydronaph(2,3-d)oxazol-2-carboxylate.

EXAMPLE 6

By using appropriate substituted phenols, a wide variety of other compounds in the same series can be prepared by the same procedure. Examples of such compounds are:

5,6,7,8-Tetrahydro-4-chloronaphth[2,3-d]oxazole-2-carboxylic acid Ethyl oxazolo[4,5-f]indane-2-carboxylate Ethyl 5,6,7,8-tetrahydro-4-trifluoromethyl naphth[2,3-d]oxazole-2-carboxylate

We claim:

1. A compound useful as an antiallergic agent of the structure

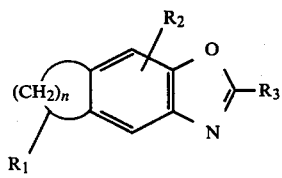

and salts thereof;
wherein
n is 3, 4, or 5
$R_1$ is hydrogen or $C_1$-$C_6$ alkyl,
$R_2$ is hydrogen, $C_1$-$C_6$ alkyl, hydroxyl, $C_1$-$C_6$ alkoxy, cyano, phenyl, carboxyl, tetrazole, or halogen,
$R_3$ is tetrazole, carboxamide or

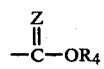

wherein
Z is oxygen, sulfur, or NH and
$R_4$ is H, alkali metal, ammonium, $C_1$-$C_6$ alkyl, $C_1$-$C_6$ alkoxy $C_1$-$C_6$ alkyl, $C_6$ aryl, or $C_6$ aryl $C_1$-$C_6$ alkyl.

2. The compound of claim 1 wherein the alkyl groups contain 1-6 carbon atoms.

3. The compound of claim 1 wherein n is 4.

4. The compound of claim 1 wherein
n is 4,
$R_1$ is hydrogen,
$R_2$ is hydrogen or an alkyl having 1 to 6 carbon atoms,
$R_3$ is tetrazole or

5. A method of treatment of allergies of a sensitized human and animal which comprises administering an effective amount of the compound of claim 1.

6. A method of treatment of allergies of a sensitized human and animal which comprises administering an effective amount of the compound of claim 4.

7. A method of treatment of allergies of sensitized humans and animals which comprises administering an effective amount of a tetrahydronapth (2,3-d) oxazole.

8. The compound of claim 1 wherein the compound is Ethoxyethyl-5,6,7,8-tetrahydronaphth[2,3-d]oxazole-2-carboxylate.

9. The compound of claim 1 wherein the compound is Sodium 5,6,7,8-tetrahydronaph[2,3-d]oxazole-2-carboxylate.

10. The compound of claim 1 wherein the compound is 2-(5-tetrazolyl)-5,6,7,8-tetrahydronaph[2,3-d]oxazole.

11. The compound of claim 1 wherein the compound is ethoxyethyl-9-propyl-5,6,7,8-tetrahydronaph (2,3-d) oxazol-2-carboxylate.

12. A compound useful as an antiallergic agent of the group:
(a) ethoxyethyl-5,6,7,8-tetrahydronaphth[2,3-d]oxazole-2-carboxylate;
(b) sodium 5,6,7,8-tetrahydronaph[2,3-d]oxazole-2-carboxylate;
(c) 2-(5-tetrazolyl)-5,6,7,8-tetrahydronaph[2,3-d]oxazole; and
(d) ethoxyethyl-9-propyl-5,6,7,8-tetrahydronaph(2,3-d) oxazole-2-carboxylate.

* * * * *